United States Patent
Yamagami et al.

(10) Patent No.: US 7,518,003 B2
(45) Date of Patent: Apr. 14, 2009

(54) PRODUCTION PROCESS OF TETRAHYDROPYRAN COMPOUND AND TETRAHYDROPYRAN COMPOUND PRODUCED BY THE PRODUCTION PROCESS

(75) Inventors: Isao Yamagami, Kawasaki (JP); Hiroshi Yasuda, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 13 days.

(21) Appl. No.: 11/791,944

(22) PCT Filed: Dec. 5, 2005

(86) PCT No.: PCT/JP2005/022706

§ 371 (c)(1),
(2), (4) Date: May 31, 2007

(87) PCT Pub. No.: WO2006/062211

PCT Pub. Date: Jun. 15, 2006

(65) Prior Publication Data

US 2008/0139828 A1    Jun. 12, 2008

Related U.S. Application Data

(60) Provisional application No. 60/635,611, filed on Dec. 14, 2004.

(30) Foreign Application Priority Data

Dec. 6, 2004    (JP) ............................. 2004-352914

(51) Int. Cl.
*C07D 309/04*    (2006.01)

(52) U.S. Cl. ...................................... 549/356; 549/416
(58) Field of Classification Search ................ 549/356, 549/416
See application file for complete search history.

(56) References Cited

U.S. PATENT DOCUMENTS 6,403,845 B1    6/2002    Pfeffinger et al.

FOREIGN PATENT DOCUMENTS

| EP | 0 219 091 A | 4/1987 |
|---|---|---|
| JP | 62-93285 A | 4/1987 |
| JP | 1-290640 A | 11/1989 |
| JP | 02-167274 A | 6/1990 |
| JP | 2001-64219 A | 3/2001 |
| SU | 717 052 A1 | 2/1980 |

OTHER PUBLICATIONS

Raymond I. Longley, Jr., et al. "Some Reactions of 2-Alkoxy-3,4-dihydro-2H-pyrans", J. Am. Chem. Soc., 1952, pp. 2012-2015, vol. 74, XP002367640.

*Primary Examiner*—Bernard Dentz
(74) *Attorney, Agent, or Firm*—Sughrue Mion, PLLC

(57) ABSTRACT

The invention provides a production process of a tetrahydropyran compound, characterized by allowing 3,4-dihydro-2-alkoxy-2H-pyran compound or tetrahydro-2-alkoxy-2H-pyran compound which can be easily prepared through reaction between acrolein and alkylvinylether, with hydrogen in the presence of a catalyst containing an element of Groups VIII to X under acidic condition. The production process of the invention is useful for production of Grignard reaction solvent or polymer solvent and intermediate of organic compound.

14 Claims, No Drawings

US 7,518,003 B2

PRODUCTION PROCESS OF TETRAHYDROPYRAN COMPOUND AND TETRAHYDROPYRAN COMPOUND PRODUCED BY THE PRODUCTION PROCESS

CROSS-REFERENCE TO THE RELATED APPLICATIONS

This is an application filed pursuant to 35 U.S.C. Section 111(a) with claiming the benefit of U.S. provisional application Ser. No. 60/635,611 filed Dec. 14, 2004 under the provision of 35 U.S.C. 111(b), pursuant to 35 U.S.C. Section 119(e) (1).

TECHNICAL FILED

The present invention relates to a production process of a tetrahydropyran compound and a tetrahydropyran compound obtained by the production process. More specifically, the invention relates to a production process of a tetrahydropyran compound, which comprises a step of allowing 3,4-dihydro-2-alkoxy-2H-pyran compound or a tetrahydro-2-alkoxy-2H-pyran compound to react with hydrogen.

The tetrahydropyran compound obtained by the present invention is useful as a solvent, particularly, as a Grignard solvent, as a solvent for polymer or as an organic intermediate.

BACKGROUND ART

Conventionally, as methods for synthesizing a tetrahydropyran compound, a method of synthesizing a tetrahydropyran where 3,4-dihydro-2-butoxy-2H-pyran is catalytically hydrogenated by using a nickel catalyst is known (Journal of American Chemical Society Vol. 74, Page 2012 (1952)). However, this method has disadvantages in that the selectivity of tetrahydropyran compound is low in this method and that as a result, 5-butoxy pentanol is generated in a large amount.

Also, a method of synthesizing a tetrahydropyran compound through catalytic hydrogenation of 3,4-dihydro-2-alkoxy-2H-pyran compound or tetrahydro-2-alkoxy-2H-pyran compound by using tetrahydrofuran (THF) as a solvent and palladium activated carbon as a catalyst is disclosed (JP S62-093285 A). However, the reaction conditions for this method is reaction temperature of 150° C., reaction time of 20 hours and reaction pressure of 200 bar (approx. 20 MPa), which is too demanding to put into industrial application. Therefore, more milder reaction conditions are desirable.

Further, it is disclosed that tetrahydropyran (THP) is generated as byproduct in a method of synthesizing 1,5-pentanediol through hydrogenation of 3,4-dihydro-2-alkoxy-2H-pyran in the presence of water and a catalyst (JP 2001-64219 A). However, the method, which preferentially generates 1,5-pentanediol, is not preferred as a production process of a tetrahydropyran compound.

As examples of other methods of producing tetrahydropyran compounds, cyclization-dehydration reaction of a corresponding 1,5-pentanediol (JP H02-167274 A) and reduction reaction of a corresponding lactone (JP H01-290640 A) have been reported as available. However, these methods also involves problems of low yield of a tetrahydropyran compound and low selectivity and there is an increasing demand for a production method with a higher yield and a higher selection rate.

DISCLOSURE OF THE INVENTION

An object of the present invention is to solve problems in conventionally known production process of a tetrahydropyran compound and provide a production process which enables production of a tetrahydropyran compound under milder reaction conditions in an easier manner.

Another object of the present invention is to provide a production process of a tetrahydropyran compound where compounds as starting materials which are more inexpensive and more available can be used.

The present inventors made keen efforts for solving the above problems. As a result, they have found out that, with respect to a production process where a tetrahydropyran compound is produced by allowing 3,4-dihydro-2-alkoxy-2H-pyran compound or tetrahydro-2-alkoxy-2H-pyran compound to react with hydrogen in the presence of a catalyst, by carrying out the reaction under acidic condition, reaction conditions in producing a tetrahydropyran compound can be milder with relatively low temperature and pressure, and thus completed the present invention.

That is, the present invention relates to the following production process of a tetrahydropyran compound and tetrahydropyran compound.

1. A production process of a tetrahydropyran compound represented by formula (2), wherein 3,4-dihydro-2-alkoxy-2H-pyran compound represented by formula (1)

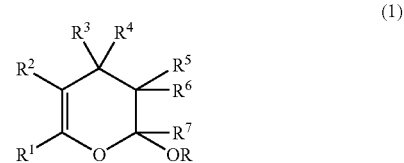

(in the formula, R represents an aliphatic hydrocarbon group having 1 to 8 carbon atoms which may have a substituent or a hydrocarbon group having an aromatic group having 6 to 12 carbon atoms which may have a substituent $R^1$ to $R^7$ each independently represents a hydrogen atom, an aliphatic hydrocarbon group having 1 to 8 carbon atoms which may have a substituent, an aromatic group having 6 to 12 carbon atoms which may have a substituent, an alkoxy group, an amino group or a substituted amino group.)

is reacted with hydrogen in the presence of a catalyst under acidic condition.

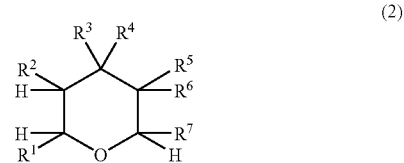

(all the symbols in the formula have the same meanings as defined above).

2. A production process of a tetrahydropyran compound represented by formula (4), wherein tetrahydro-2-alkoxy-2H-pyran compound represented by formula (4)

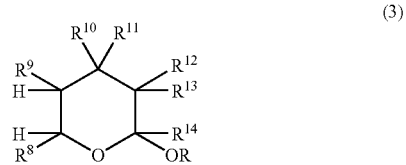

(In the formula, R represents an aliphatic hydrocarbon group having 1 to 8 carbon atoms which may have a substituent or a hydrocarbon group having an aromatic group having 6 to 12 carbon atoms which may have a substituent. $R^8$ to $R^{14}$ each independently represents a hydrogen atom, an aliphatic hydrocarbon group having 1 to 8 carbon atoms which may have a substituent, an aromatic group having 6 to 12 carbon atoms which may have a substituent, an alkoxy group, an amino group or a substituted amino group.) is reacted with hydrogen in the presence of a catalyst under acidic condition.

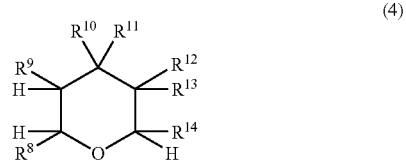

3. The production process of a tetrahydropyran compound according to 1, wherein the 3,4-dihydro-2-alkoxy-2H-pyran compound is a compound selected from a group consisting of 3,4-dihydro-2-methoxy-2H-pyran, 3,4-dihydro-2-ethoxy-2H-pyran, 3,4-dihydro-2-n-propoxy-2H-pyran, 3,4-dihydro-2-isopropoxy-2H-pyran, 3,4-dihydro-2-isobutoxy-2H-pyran and 3,4-dihydro-2-n-butoxy-2H-pyran.

4. The production process of a tetrahydropyran compound according to 2, wherein the tetrahydro-2-alkoxy-2H-pyran compound is selected from a group consisting of tetrahydro-2-methoxy-2H-pyran, tetrahydro-2-ethoxy-2H-pyran, tetrahydro-2-n-propoxy-2H-pyran, tetrahydro-2-isopropoxy-2H-pyran, tetrahydro-2-isobutoxy-2H-pyran and tetrahydro-2-n-butoxy-2H-pyran.

5. The production process of a tetrahydropyran compound according to 1 or 2, wherein the hydrogen is at least one selected from a group consisting of electrolytic hydrogen and petroleum-based hydrogen 6. The production process of a tetrahydropyran compound according to 1 or 2, wherein the acidic condition is within a pH range of 1 to 6.

7. The production process of a tetrahydropyran compound according to 1, 2 or 6, wherein the acidic condition is prepared by addition of at least one compound selected from a group consisting of sulfuric acid, sodium hydrogensulfate, potassium hydrogensulfate, p-toluene sulfonic acid, heteropoly acid, sodium dihydrogen phosphate and acidic ion-exchange resin.

8. The production process of a tetrahydropyran compound according to 1 or 2, wherein the reaction is carried out under a pressure of 1 kPa to 10 MPa.

9. The production process of a tetrahydropyran compound according to 1 or 2, wherein the catalyst used contains an element of Groups VIII to X.

10. The production process of a tetrahydropyran compound according to 9, wherein the element of Groups VIII to X is at least one kind selected from the group consisting of nickel, ruthenium, palladium and platinum.

11. The production process of a tetrahydropyran compound according to 1, 2, 9 or 10, wherein the catalyst is a supported catalyst.

12. The production process of a tetrahydropyran compound according to 1, comprising the following procedures of step-1 to step-3:

Step-1: reacting 3,4-dihydro-2-alkoxy-2H-pyran compound represented by formula (1) with hydrogen in the presence of a catalyst

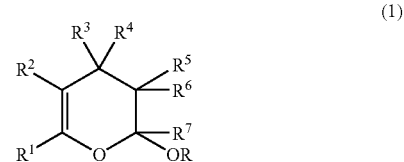

(all the symbols in the formula have the same meanings as defined in 1)

to thereby obtain a mixture as a reaction product containing a tetrahydro-2-alkoxy-2H-pyran compound represented by formula (5)

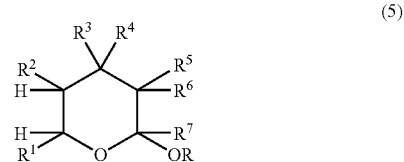

(all the symbols in the formula have the same meanings as defined above)

Step-2: adding an acid to the reaction mixture product, and

Step-3: reacting the acidic mixture product with hydrogen in the presence of a catalyst to thereby produce a reaction product containing a tetrahydropyran compound represented by formula (2).

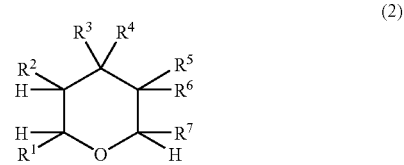

(all the symbols in the formula have the same meanings as defined above).

13. The production process of a tetrahydropyran compound according to 12, wherein 3,4-dihydro-2-alkoxy-2H-pyran compound obtained by reacting a compound represented by formula (6)

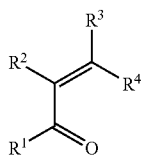
(6)

(all the symbols in the formula have the same meanings as defined in 12)

with a compound represented by formula (7)

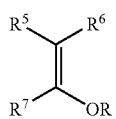
(7)

(all the symbols in the formula have the same meanings as defined in 12).

14. The production process of a tetrahydropyran compound according to 13, wherein a compound represented by formula (6) is allowed to react with a compound represented by formula (7) under increased pressure.

15. A tetrahydropyran compound which is obtained by the production process described in any one of 1 to 11.

16. A tetrahydropyran compound which is obtained by the production process described in 12 to 14.

BEST MODE FOR CARRYING OUT THE INVENTION

The present invention is specifically explained below.

The invention (1) is a production process of a tetrahydropyran compound represented by formula (2), wherein 3,4-dihydro-2-alkoxy-2H-pyran compound represented by formula (1)

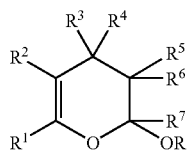
(1)

(in the formula, R represents an aliphatic hydrocarbon group having 1 to 8 carbon atoms which may have a substituent or a hydrocarbon group having an aromatic group having 6 to 12 carbon atoms which may have a substituent. $R^1$ to $R^7$ each independently represents a hydrogen atom, an aliphatic hydrocarbon group having 1 to 8 carbon atoms which may have a substituent, an aromatic group having 6 to 12 carbon atoms which may have a substituent, an alkoxy group, an amino group or a substituted amino group.) is reacted with hydrogen in the presence of a catalyst under acidic condition.

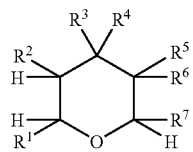
(2)

(all the symbols in the formula have the same meanings as defined above).

The 3,4-dihydro-2-alkoxy-2H-pyran compound used in Invention (I) can be produced by a conventionally known method. For example, 3,4-dihydro-2-alkoxy-2H-pyran can be prepared by reaction between acrolein and alkylvinylether (Journal of American Chemical Society Vol. 72, Page 3079 (1950)), Journal of Molecular Catalysis, Vol. 72, Page 209 (1992)).

When the reaction is performed under increased pressure, side-reaction such as polymerization of a compound represented by formula (7) can be suppressed and therefore, the production yield of 3,4-dihydro-2-alkoxy-2H-pyran compound can be enhanced. The increased pressure is prepared by using an inert gas such as nitrogen and is preferably 0.2 MPa or more.

The 3,4-dihydro-2-alkoxy-2H-pyran compound used in Invention (I) is not particularly limited as far as the compound has a structure represented by formula (1). Here, in terms of production yield and selectivity, it is preferable that $R^1$ to $R^7$ in the formula each independently be a hydrogen atom, an aliphatic hydrocarbon group having 1 to 8 carbon atoms which may have a substituent or an aromatic group having 6 to 12 carbon atoms which may have a substituent, more preferably an aliphatic hydrocarbon group having 1 to 8 carbon atoms which may have a substituent. When an alkoxy group or an amino group is present in 3,4-dihydro-2-alkoxy-2H-pyran compound, although reaction can proceed, more byproducts are generated.

Further, R in the formula is preferably R which represents an aliphatic hydrocarbon group having 1 to 8 carbon atoms which may have a substituent, more preferably an aliphatic hydrocarbon group having 1 to 4 carbon atoms which may have a substituent. In producing a tetrahydropyran compound from 3,4-dihydro-2-alkoxy-2H-pyran compound, R in the formula is generated as an alcohol having a structure of ROH, along with generation of the tetrahydropyran compound. Therefore, the smaller the molecular weight of R, the higher the productivity of the tetrahydropyran compound. Further, use of an alcohol non-azeotropic with the tetrahydropyran compound makes preparation of the tetrahydropyran compound easier. In a case where the tetrahydropyran compound is tetrahydropyran (THP), a butanol such as n-butanol or isobutanol is preferably used.

Examples of 3,4-dihydro-2-alkoxy-2H-pyran compound used in Invention (I) include 3,4-dihydro-2-methoxy-2H-pyran, 3,4-dihydro-2-ethoxy-2H-pyran, 3,4-dihydro-2-n-propoxy-2H-pyran, 3,4-dihydro-2-isopropoxy-2H-pyran, 3,4-dihydro-2-isobutoxy-2H-pyran, 3,4-dihydro-2-n-butoxy-2H-pyran, 3,4-dihydro-2-methoxy-6-methyl-2H-pyran, 3,4- dihydro-2-methoxy-5-methyl-2H-pyran, 3,4-dihydro-2-methoxy-4-methyl-2H-pyran and 3,4-dihydro-2-methoxy-4-phenyl-2H-pyran.

Hydrogen used in Invention (I) is not particularly limited and any of electrolytic hydrogen and petroleum-based hydrogen may be used. Here, what is meant by the term "electrolytic hydrogen" here is hydrogen prepared by electrolysis of water. What is meant by the term "petroleum-based hydrogen" is hydrogen prepared by naphtha cracking. Hydrogen diluted with an inert gas such as nitrogen or argon may also be used.

In Invention (I), it is necessary to carry out the reaction under acidic condition. Generally, the acidic reaction condition is prepared by allowing an acid to be present in the reaction system. As the acidic condition, the pH of the reaction mixture is within a range of −1 to 6, preferably within a range of 0 to 4, more preferably within a range of 1 to 3. When the pH is lower than −1, polymerization of raw materials or intermediates proceeds, which leads to decrease in production yield. When the pH exceeds 6 and is around neutral pH value, no effects can be obtained by adding an acid, which results in low yield.

The pH values can be measured by using a commercially available pH meter (e.g. pH METER D-12 manufactured by HORIBA, Ltd.). In order to measure the pH value more simply, the measurement may be performed by using a commercially available pH-test paper (e.g. pH-test paper 1.0 to 14.0 manufactured by Whatman plc.).

Any Bronsted acid as defined as a proton donor and any Lewis acid defined as an electron pair acceptor (quoted by KAGAKU DAIJITEN published by KYORITSU SHUPPAN CO., LTD.) may be used without any limitation. For example, sulfuric acid, sodium hydrogensulfate, potassium hydrogensulfate, p-toluene sulfonic acid, heteropoly acid or sodium dihydrogen phosphate can be preferably used.

Also, an acidic ion-exchange resin or a solid acid such as acid clay can be preferably used.

The molar ratio of acid and raw material used in Invention (I) is not particularly limited. Usually, the acid equivalent based on the amount of the raw materials is preferably from 0.0001 to 10 mol %, more preferably from 0.001 to 5 mol %, most preferably from 0.01 to 1 mol %.

The catalyst used in Invention (I) is not particularly limited as far as the catalyst has an ability to hydrogenate. Preferred examples of catalyst include catalysts containing elements of Groups VIII to X in the Periodic Table.

Examples of elements belonging to Groups VIII to X include cobalt, nickel, ruthenium, iridium, palladium and platinum. Preferred among these are nickel, ruthenium, palladium and platinum.

It is more preferable that these elements be supported by a support when used, for the purpose of increasing the surface area of the catalyst. Examples of support include activated carbon, silica, alumina, titania and zeolite.

Examples of the above catalyst include palladium supported on activated carbon, platinum Supported on activated carbon, palladium supported on silica, palladium supported on alumina and palladium supported on titania.

It is preferable that the amount of the element(s) supported on or in the catalyst be from 0.01 to 20 mass %, more preferably from 0.1 to 10 mass %, most preferably 0.5 to 5 mass % based on the total amount of the catalyst.

An amount of the element less than 0.01 mass % leads to increase in the amount of the supported catalyst and reducing handleability or to increase in the amount of reaction products adsorbed onto the catalyst, although it depends on the reactivity, which is not preferred. On the other hand, the amount of the element exceeding 20 mass % is not preferred either, in that an excessive amount does not lead to relative increase in the surface area and enhancement in production yield.

Preparation method of the catalyst used in Invention (I) is not particularly limited. Specific examples thereof include a method of impregnating a supported catalyst with a solution or a suspension in which nitrate salt, chloride salt or the like containing catalyst component element(s) is dissolved or suspended in water or an organic solvent. Subsequently, the element is reduced to zero valence state through wet reduction using hydrazine or dry reduction using hydrogen, to thereby prepare a catalyst. In this case, not all the supported elements have to be in zero valence state. Detailed explanation is included in "Gensobetsu Shokubai Binran" (=Handbook of catalyst for each element) published on 25 Apr. 1967 by CHIJIN SHOKAN CO., LTD.

With respect to the molar ratio of the catalyst to raw materials in Invention (I), the catalyst amount is preferably from 0.0001 to 1 mol %, more preferably 0.001 mol % to 0.5 mol % based on the total amount of the raw materials, in a case where the reaction is performed in batch processing system. If the catalyst amount is less than 0.0001 mol %, the reactivity will decrease. On the other hand, a catalyst amount exceeding 1 mol % does not contribute to improvement in reaction rate.

The reaction temperature in Invention (I) is not particularly limited. The temperature is preferably from 20° C. to 160° C., more preferably from 70° C. to 130° C. If the temperature is lower than 20° C., the reaction speed is extremely low while the reaction condition with the temperature exceeds 160° C. is hard to be put into industrial use.

The reaction pressure in Invention (I) is not particularly limited. Generally, it is preferable that the pressure be from 1 kPa to 10 MPa, more preferably, 0.2 MPa to 2.0 MPa. The pressure of less than 1 kPa is disadvantageous in that the reaction rate becomes low. The pressure exceeding 10 MPa is disadvantageous in that huge apparatuses are required.

In Invention (I), use of solvent is not necessary. However, in a case where a reaction raw material is solid or for the purpose of dissolving an acid compound or alleviating reaction temperature increase due to rapid heat generation, solvent may be used. The solvent is not particularly limited as far as the solvent is liquid at the reaction temperature and has resistance to hydrogenation, and examples thereof include methanol, ethanol, isobutanol, n-butanol, ethylene glycol, 1,5-pentanediol, tetrahydrofuran, tetrahydropyran, water, toluene, hexane and ethyl acetate.

The tetrahydropyran compound produced by Invention (I) can be isolated by a generally employed method. Specific examples of the method include distillation, recrystallization and spray-drying.

Invention (II) is a production process of a tetrahydropyran compound by allowing tetrahydro-2-alkoxy-2H-pyran compound represented by formula (3) to react with hydrogen in the presence of catalyst to thereby produce a tetrahydropyran compound represented by formula (4), wherein the reaction is carried out under acidic condition.

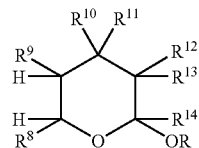

(3)

(In the formula, R represents an aliphatic hydrocarbon group having 1 to 8 carbon atoms which may have a substituent or a hydrocarbon group having an aromatic group having 6 to 12 carbon atoms which may have a substituent. $R^8$ to $R^{14}$ each independently represents a hydrogen atom, an aliphatic hydrocarbon group having 1 to 8 carbon atoms which may have a substituent, an aromatic group having 6 to 12 carbon atoms which may have a substituent, an alkoxy group, an amino group or a substituted amino group.)

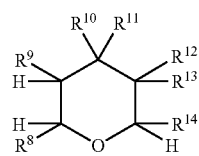

(4)

(All the symbols in the formula have the same meanings as defined above.)

A tetrahydro-2-alkoxy-2H-pyran compound used in Invention (II) can be prepared by a conventionally known method. Specifically, for example, the compound can be obtained by hydrogenating 3,4-dihydro-2-alkoxy-2H-pyran (JP-A-S62-93285).

The tetrahydro-2-alkoxy-2H-pyran compound used in Invention (II) is not particularly limited as far as the compound has a structure represented by formula (3). In terms of production yield and selectivity, $R^8$ to $R^{14}$ in the formula each independently is preferably a hydrogen atom, an aliphatic hydrocarbon having 1 to 8 carbon atoms which may have a substituent or an aromatic group having 6 to 12 carbon atoms which may have a substituent, more preferably an aliphatic hydrocarbon having 1 to 8 carbon atoms which may have a substituent. When an alkoxy group or an amino group is present in tetrahydro-2-alkoxy-2H-pyran compound, although reaction can proceed, more byproducts are generated.

Moreover, it is more preferable that R in the formula be an aliphatic hydrocarbon having 1 to 8 carbon atoms which may have a substituent, even more preferably an aliphatic hydrocarbon having 1 to 4 carbon atoms which may have a substituent. When a tetrahydropyran compound is produced from tetrahydro-2-alkoxy-2H-pyran compound, R in the formula is generated as an alcohol represented by a structure ROH, together with generation of the tetrahydropyran compound. Accordingly, the smaller the molecular weight of R, the higher the productivity of the tetrahydropyran compound.

Examples of tetrahydro-2-alkoxy-2H-pyran compound used in Invention (II) include tetrahydro-2-methoxy-2H-pyran, tetrahydro-2-ethoxy-2H-pyran, tetrahydro-2-n-propoxy-2H-pyran, tetrahydro-2-isopropoxy-2H-pyran, tetrahydro-2-isobutoxy-2H-pyran, tetrahydro-2-n-butoxy-2H-pyran, tetrahydro-2-methoxy-6-methyl-2H-pyran, tetrahydro-2-methoxy-5-methyl-2H-pyran, tetrahydro-2-methoxy-4-methyl-2H-pyran and tetrahydro-2-methoxy-4-phenyl-2H-pyran.

Hydrogen used in Invention (II) is the same as mentioned in Invention (I).

In Invention (II), the reaction needs to be carried out under acidic condition. The acidic condition is prepared by allowing an acid to be present in the reaction system, as in Invention (I). Examples of the acidic condition and the acid employed in Invention (II) are the same as those mentioned in Invention (I).

The molar ratio of the acid to the raw materials used in Invention (II) is the same as in Invention (I).

The catalyst may be used in Invention (II), as in Invention (I).

The preparation method of the catalyst used in Invention (II) is the same as in Invention (I).

The molar ratio of the catalyst to the raw materials used in Invention (II) is within the same range as defined in Invention (I).

The reaction temperature and pressure used in Invention (II) is within the same range as defined in Invention (I).

In Invention (II), use of solvent is not necessary. However, solvent mentioned un relation to Invention (I) may be used.

The tetrahydropyran compound produced in Invention (II) can be isolated by distillation, recrystallization or spray-drying, as in Invention (I).

Invention (III) is a production process of a tetrahydropyran compound comprising the following steps:

Step-1: reacting 3,4-dihydro-2-alkoxy-2H-pyran compound represented by formula (1) with hydrogen in the presence of a catalyst to thereby obtain a mixture as a reaction product containing a tetrahydro-2-alkoxy-2H-pyran compound represented by formula (5)

Step-2: adding an acid to the reaction mixture product, and

Step-3: reacting the acidic reaction mixture product with hydrogen in the presence of a catalyst to thereby produce a reaction product containing a tetrahydropyran compound represented by formula (2).

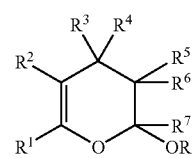

(1)

(In the formula, R represents an aliphatic hydrocarbon group having 1 to 8 carbon atoms which may have a substituent or a hydrocarbon group having an aromatic group having 6 to 12 carbon atoms which may have a substituent. $R^1$ to $R^7$ each independently represents a hydrogen atom, an aliphatic hydrocarbon group having 1 to 8 carbon atoms which may have a substituent, an aromatic group having 6 to 12 carbon atoms which may have a substituent, an alkoxy group, an amino group or a substituted amino group.)

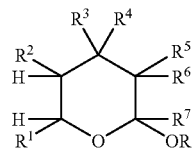

(5)

(All the symbols in the formula have the same meanings as defined above.)

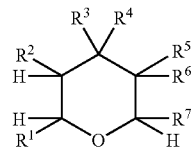

(2)

(All the symbols in the formula have the same meanings as defined above.)

Here, the compound represented by formula (1) may be a 3,4-dihydro-2-alkoxy-2H-pyran compound produced through reaction between a compound represented by formula (6) and a compound represented by formula (7) by the method described in Journal of American Chemical Society Vol. 72, Page 3079 (1950)).

When reaction between compound represented by formula (6) and compound represented by formula (7) is performed under increased pressure, side-reaction such as polymerization of a compound represented by formula (6) can be suppressed.

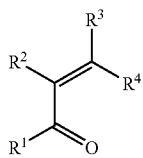

(6)

(All the symbols in the formula have the same meanings as defined above.)

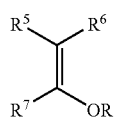

(7)

(All the symbols in the formula have the same meanings as defined above.)

Invention (IV) is a tetrahydropyran compound produced by production process according to any one of Invention (I) to (III).

EXAMPLES

Hereinafter, the present invention is illustrated with reference to representative examples. However, the invention is by no means limited to the examples.

In analysis of each component in Examples, a gas chromatography apparatus (6890N, manufactured by Agilent Technologies, Inc.) was used and DB-1 (length 30 m, diameter 0.32 mm and film thickness 1 μm) manufactured by J&W Scientific Inc. was used as a analysis column.

Example 1

In a 100 mL-volume microautoclave made of stainless steel, 5.71 g of 3,4-dihydro-2-methoxy-2H-pyran (DHMP) (reagent manufactured by Tokyo Kasei Kogyo Co., Ltd.), 0.053 g of 5 mass % palladium/activated carbon powder (Pd/C)(K-type manufactured by N. E. Chemcat Corp.) and 0.069 g of sodium hydrogen sulfate hydrate were placed and mixed with each other. The pH of the mixture measured by a pH test paper manufactured by Whatman plc. was 1. The inside of the reactor was purged with hydrogen, and 0.8 MPa of hydrogen was introduced. The mixture was reacted at 130° C. for 4 hours. During the reaction, hydrogen was added so that 0.8 MPa was maintained.

As a result of analysis on the reaction mixture after the reaction, the yield of tetrahydropyran (THP) was 50%. As a byproduct, tetrahydro-2-methoxy-2H-pyran (THMP) was generated at a yield of 20% and methanol was generated at a yield of 55% based on the amount of the raw material.

Example 2

In a 100 mL-volume autoclave made of stainless steel, 23.17 g of 3,4-dihydro-2-methoxy-2H-pyran (DHMP) and 0.42 g of 5 mass % palladium/activated carbon powder (Pd/C) were placed. The reactor was purged with hydrogen, and 0.8 MPa of hydrogen was introduced. This was stirred at a room temperature and hydrogen was continuously introduced into the reactor so that the pressure 0.8 MPa was maintained during the reaction. In this step, the amount of the hydrogen gas introduced into the reactor was 4737 ml (Step-1). After 1.5 hour, DHMP as raw material was not detected. Tetrahydro-2-methoxy-2H-pyran (THMP) was produced at a yield of 96%. After adding 1.10 g of sodium hydrogen sulfate hydrate to the reaction mixture, the pH of the reaction mixture measured was 1 (Step-2). As in Step-1, the reactor was pressurized to 0.8 MPa with hydrogen. Reaction was performed at 70° C. for 2 hours, 100° C. for 2 hours, and then 130° C. for 1.5 hours, while continuously introducing hydrogen into the reactor. In this step, the amount of the hydrogen gas introduced into the reactor was 3989 ml (Step-3).

As a result of the reaction mixture after the reaction, the yield of tetrahydropyran (THP) was 82%. THMP was generated at a yield of 7% and methanol was generated at a yield of 80% based on the amount of the raw material.

Example 3

The same procedures were carried out as in Example 2 except that 23.79 g of 3,4-dihydro-2-methoxy-2H-pyran (DHMP) and 0.21 g of 5 mass % palladium/activated carbon powder (Pd/C) were used and that 0.38 g of p-toluene sulfonic acid monohydrate was used instead of sodium hydrogen sulfate hydrate. As a result, the amount of the hydrogen gas introduced into the reactor in Step-1 was 4872 ml. The yield of tetrahydro-2-methoxy-2H-pyran (THMP) in Step-1 was 97%. The pH of the reaction mixture in Step-2 was 1. Further, the amount of the hydrogen gas introduced into the reactor in Step-3 was 3418 ml. The yield of the obtained tetrahydropyran (THP) was 70%, the yield of the by-produced THMP was 20%, and the yield of the generated methanol was 67%.

Example 4

Reduction reaction was performed by carrying out the same procedures as in Example 2 except that 23.46 g of 3,4-dihydro-2-butoxy-2H-pyran (DHBP) was used instead of 3,4-dihydro-2-methoxy-2H-pyran (DHMP). As a result, the yield of tetrahydropyran (THP) was 95%. Tetrahydro-2-butoxy-2H-pyran (THBP) was not detected while butanol was generated at a yield of 96% based on raw material.

Example 5

Reduction reaction was performed by carrying out the same procedures as in Example 2 except that 33.66 g of 3,4-dihydro-2-butoxy-4-methyl-2H-pyran (DHBMeP) was used instead of 3,4-dihydro-2-methoxy-2H-pyran (DHMP). As a result, the yield of tetrahydro-4-methyl-2H-pyran (THMeP) was 93%. As a byproduct, tetrahydro-2-butoxy-4-methyl-2H-pyran (THBMeP) was generated at a yield of 1%, and butanol was generated at a yield of 90% based on the raw material.

Example 6

In a 100 mL-volume autoclave made of stainless steel, 23.25 g of tetrahydro-2-methoxy-2H-pyran (THMP), 0.21 g of 5 mass % palladium/activated carbon powder (Pd/C) and 1.10 g of sodium hydrogen sulfate hydrate were placed and mixed with each other. The pH of the reaction mixture was 1. The inside of the reactor was purged with hydrogen and 0.8 MPa of hydrogen was introduced therein. Reaction was performed at 70° C. for 2 hours and then 130° C. for 1.5 hours, while continuously introducing hydrogen into the reactor. During the reaction, hydrogen was introduced so that the pressure of 0.8 MPa was maintained. In this reaction, the amount of the hydrogen gas introduced into the reactor was 3989 ml.

As a result of analysis on the components of the reaction mixture after the reaction, the yield of tetrahydropyran (THP) was 76%. THMP, as a raw material remaining unreacted, was detected at a yield of 10% and methanol was generated at a yield of 78% based on the amount of the raw material.

Example 7

Reduction reaction was performed by carrying out the same procedures as in Example 6 except that 32.30 g of tetrahydro-2-butoxy-2H-pyran (THBP) was used instead of tetrahydro-2-methoxy-2H-pyran (THMP). As a result of analysis on the reaction mixture after the reaction, the yield of tetrahydropyran (THP) was 94%. THBP was not detected and butanol was generated at a yield of 92% based on the amount of raw material.

Example 8

Reduction reaction was performed by carrying out the same procedures as in Example 2 except that 23.22 g of 3,4-dihydro-2-methoxy-2H-pyran (DHMP) was used and that reaction pressure was 2.0 MPa. As a result of analysis on the reaction mixture after the reaction, the yield of tetrahydropyran (THP) was 94%. Tetrahydro-2-methoxy-2H-pyran (THMP) was not detected and methanol was generated at a yield of 92% based on the amount of the raw material.

Example 9

In a 100 mL-volume autoclave made of stainless-steel, 5.81 g of tetrahydro-2-methoxy-2H-pyran (THMP), 0.053 g of 5 mass % palladium/activated carbon powder (Pd/C) and 0.092 g of an ion-exchange resin (Diaion PK-216, modified product of H-type) were placed and mixed with each other. The pH of the reaction mixture was 4. The inside of the reactor was purged with hydrogen and 0.8 MPa of hydrogen was introduced therein. Reaction was performed at 100° C. for 4 hours. During the reaction, hydrogen was introduced so that the pressure of 0.8 MPa was maintained. As a result of analysis on the reaction mixture after the reaction, the yield of tetrahydropyran (THP) was 70%. THMP, as a raw material remaining unreacted, was detected at 15% based on the total use amount and methanol was generated at a yield of 71% based on the amount of the raw material.

Comparative Example 1

In a 100 mL-volume autoclave made of stainless-steel, 23.42 g of 3,4-dihydro-2-methoxy-2H-pyran (DHMP) and 0.42 g of 5 mass % palladium/activated carbon powder (Pd/C) were placed. The inside of the reactor was purged with hydrogen and 0.8 MPa of hydrogen was introduced therein. Then, reaction was performed at room temperature for 1 hour. During the reaction, hydrogen was introduced so that the pressure of 0.8 MPa was maintained. When 4793 ml of hydrogen was absorbed, absorption of hydrogen stopped. Reaction was performed at a higher temperature, 130° C. for 1 hour, and then 160° C. for 4 hours. The amount of the hydrogen gas introduced into the reactor after increasing the temperature was 388 ml. As a result of analysis on the reaction mixture after the reaction, the yield of tetrahydropyran (THP) was 18%. As other generated products, THMP was generated at a yield of 61% and 3,4-dihydropyran was generated at a yield of 5%. Methanol was generated at a yield of 25% based on the amount of the raw material.

Example 10

In a 100 mL-volume microautoclave made of stainless-steel, 20.9 g of methylvinylether (MVE), 16.8 g of acrolein (ACR) and 0.2 g of di-t-butylhydroxytoluene (BHT) were placed and the inside of the reactor was purged with nitrogen.

The pressure was increased to 3 MPa with nitrogen and reaction was performed at 135° C. for 12 hours. The yield of 3,4-dihydro-2-isobutoxy-2H-pyran (DHMP) was 92% (with ACR used as standard).

Comparative Example 2

In a 100 mL-volume microautoclave made of stainless-steel, 20.9 g of methylvinylether (MVE), 16.8 g of acrolein (ACR) and 0.2 g of di-t-butylhydroxytoluene (BHT) were placed and the inside of the reactor was purged with nitrogen. Reaction was performed at 135° C. for 12 hours. The yield of 3,4-dihydro-2-methoxy-2H-pyran (DHMP) was 77% (with ACR used as standard). Solid substance precipitated in the reaction solution and deposited on the surface of sidewalls and the ceiling of the microautoclave.

Example 11

In a 50 L-volume autoclave made of stainless-steel, 16.22 kg of isobutylvinylether (IBVE), 6.97 kg of acrolein (ACR) and 0.08 kg of di-t-butylhydroxytoluene (BHT) were placed and the inside of the reactor was purged with nitrogen. The pressure was increased to 3 MPa with nitrogen and reaction was performed at 135° C. for 16 hours. The yield of 3,4-dihydro-2-isobutoxy-2H-pyran (DHIBP) was 94% (with ACR used as standard). The reaction solution was subjected to distillation, to thereby obtain 17.1 kg of DHIBP (20 kPa/120° C.).

Example 12

In a 50 L-volume autoclave made of stainless-steel, 16.22 kg of butylvinylether (BVE), 6.97 kg of acrolein (ACR) and 0.08 kg of di-t-butylhydroxytoluene (BHT) were placed and the inside of the reactor was purged with nitrogen. The pressure was increased to 3 MPa with nitrogen and reaction was performed at 135° C. for 14 hours. The yield of 3,4-dihydro-2-butoxy-2H-pyran (DHBP) was 96% (with ACR used as standard). The reaction solution was subjected to distillation, to thereby obtain 17.7 kg of DHBP (20 kPa/140° C.).

Example 13

Mass Synthesis

In a 100 L-volume autoclave made of stainless-steel, 46.9 kg of 3,4-dihydro-2-isobutoxy-2H-pyran (DHIBP) and 0.64 kg of 5 mass % palladium/activated carbon powder (Pd/C) were placed. The inside of the reactor was purged with hydrogen and after hydrogen was introduced to 0.8 MPa, reaction was performed for 2.5 hours at room temperature while stirring. During the reaction, hydrogen gas was introduced so that the pressure of 0.8 MPa was maintained. After the 2 hours, no DHIBP as the raw material was detected while tetrahydro-2-isobutoxy-2H-pyran (THIBP) was generated quantitatively. To the reaction mixture, 0.42 kg of sodium hydrogen sulfate monohydrate was added and the pressure was increased to 0.8 MPa with hydrogen. Reaction was performed for 12 hours at 80° C. while continuously introducing hydrogen, and with the pressure increased to 1.2 MPa, the reaction was further performed for 4 hours. As a result of analysis on the reaction mixture after the reaction, the yield of tetrahydropyran (THP) was 92%. Also, isobutanol was generated at a yield of 93% based on the raw material.

Example 14

Isolation of THP

The reaction solution of Example 13 was filtered and introduced into a distillation can to be subjected to distillation under normal pressure.

The distillation conditions were as follows.

Packing material: Sulzer EX

Number of theoretical stages: 30

Reflux ratio: 20

In the distillation, the solution was boiled within an extent that no flooding occurred. The results are shown in Table 1.

TABLE 1

| THP | Distillation Temperature (° C.) | Amount of the distillate (kg) | GC purity (%) |
| --- | --- | --- | --- |
| Initial distillation | 72-86 | 1.8 | 99.1 |
| Main distillation | 87-88 | 19.4 | 99.9 |

Example 15

Mass Synthesis

In a 100 L-volume autoclave made of stainless-steel, 46.9 kg of 3,4-dihydro-2-butoxy-2H-pyran (DHBP) and 0.64 kg of 5 mass % palladium/activated carbon powder (Pd/C) were placed. The inside of the reactor was purged with hydrogen and after hydrogen was introduced to 0.8 MPa, reaction was performed for 2.5 hours at room temperature while stirring. During the reaction, hydrogen gas was introduced so that the pressure of 0.8 MPa was maintained. After the 2 hours, no DHBP as the raw material was detected while tetrahydro-2-butoxy-2H-pyran (THBP) was generated quantitatively. To the reaction mixture, 0.42 kg of sodium hydrogen sulfate monohydrate was added and the pressure was increased to 0.8 MPa. Reaction was performed for 10 hours at 80° C. while continuously introducing hydrogen, and with the pressure increased to 1.5 MPa, the reaction was further performed for 2 hours. As a result of analysis on the reaction mixture after the reaction, the yield of tetrahydropyran (THP) was 94%. Also, butanol was generated at a yield of 95% based on the raw material.

The reaction mixture was subjected to distillation in the same manner as in Example 14, to thereby obtain THP. The results are shown in Table 2.

TABLE 2

| THP | Distillation Temperature (°C.) | Amount of the distillate (kg) | GC purity (%) |
|---|---|---|---|
| Initial distillation | 73-86 | 2.1 | 99.1 |
| Main distillation | 87-88 | 20.3 | 99.9 |

INDUSTRIAL APPLICABILITY

The production process according to the present invention is useful in that a tetrahydropyran compound can be produced under mild reaction conditions by carrying out the reaction between 3,4-dihydro-2-alkoxy-2H-pyran and hydrogen in the presence of a catalyst under acidic condition.

The invention claimed is:

1. A production process of a tetrahydropyran compound represented by formula (2), wherein 3,4-dihydro-2-alkoxy-2H-pyran compound represented by formula (1) is reacted with hydrogen in the presence of a catalyst under acidic condition,

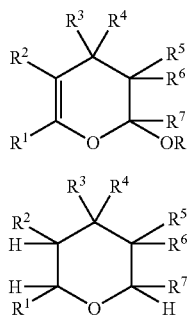

wherein R represents an aliphatic hydrocarbon group having 1 to 8 carbon atoms which may have a substituent or a hydrocarbon group having an aromatic group having 6 to 12 carbon atoms which may have a substituent $R^1$ to $R^7$ each independently represents a hydrogen atom, an aliphatic hydrocarbon group having 1 to 8 carbon atoms which may have a substituent, an aromatic group having 6 to 12 carbon atoms which may have a substituent, an alkoxy group, an amino group or a substituted amino group.

2. A production process of a tetrahydropyran compound represented by formula (4), wherein tetrahydro-2-alkoxy-2H-pyran compound represented by formula (3) is reacted with hydrogen in the presence of a catalyst under acidic condition,

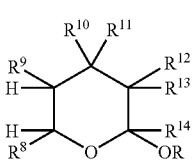

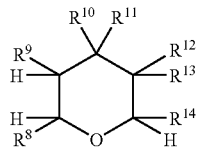

wherein R represents an aliphatic hydrocarbon group having 1 to 8 carbon atoms which may have a substituent or a hydrocarbon group having an aromatic group having 6 to 12 carbon atoms which may have a substituent. $R^8$ to $R^{14}$ each independently represents a hydrogen atom, an aliphatic hydrocarbon group having 1 to 8 carbon atoms which may have a substituent, an aromatic group having 6 to 12 carbon atoms which may have a substituent, an alkoxy group, an amino group or a substituted amino group.

3. The production process of a tetrahydropyran compound according to claim 1, wherein the 3,4-dihydro-2-alkoxy-2H-pyran compound is a compound selected from a group consisting of 3,4-dihydro-2-methoxy-2H-pyran, 3,4-dihydro-2-ethoxy-2H-pyran, 3,4-dihydro-2-n-propoxy-2H-pyran, 3,4-dihydro-2-isopropoxy-2H-pyran, 3,4-dihydro-2-isobutoxy-2H-pyran and 3,4-dihydro-2-n-butoxy-2H-pyran.

4. The production process of a tetrahydropyran compound according to claim 2, wherein the tetrahydro-2-alkoxy-2H-pyran compound is selected from a group consisting of tetrahydro-2-methoxy-2H-pyran, tetrahydro-2-ethoxy-2H-pyran, tetrahydro-2-n-propoxy-2H-pyran, tetrahydro-2-isopropoxy-2H-pyran, tetrahydro-2-isobutoxy-2H-pyran and tetrahydro-2-n-butoxy-2H-pyran.

5. The production process of a tetrahydropyran compound according to claim 1, wherein the hydrogen is at least one selected from a group consisting of electrolytic hydrogen and petroleum-based hydrogen.

6. The production process of a tetrahydropyran compound according to claim 1, wherein the acidic condition is within a pH range of 1 to 6.

7. The production process of a tetrahydropyran compound according to claim 1, wherein the acidic condition is prepared by addition of at least one compound selected from a group consisting of sulfuric acid, sodium hydrogensulfate, potassium hydrogensulfate, p-toluene sulfonic acid, heteropoly acid, sodium dihydrogen phosphate and acidic ion-exchange resin.

8. The production process of a tetrahydropyran compound according to claim 1, wherein the reaction is carried out under a pressure of 1 kPa to 10 MPa.

9. The production process of a tetrahydropyran compound according to claim 1, wherein the catalyst used contains an element of Groups VIII to X.

10. The production process of a tetrahydropyran compound according to claim 9, wherein the element of Groups VIII to X is at least one kind selected from the group consisting of nickel, ruthenium, palladium and platinum.

11. The production process of a tetrahydropyran compound according to claim 1, wherein the catalyst is a supported catalyst.

12. The production process of a tetrahydropyran compound comprising the following procedures of step-1 to step-3:

Step-1: reacting 3,4-dihydro-2-alkoxy-2H-pyran compound represented by formula (1) with hydrogen in the presence of a catalyst to thereby obtain a mixture as a reaction product containing a tetrahydro-2-alkoxy-2H-pyran compound represented by formula (5)

(1)

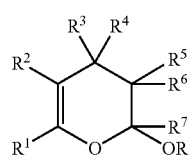

(5)

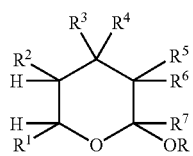

Step-2: adding an acid to the reaction mixture product, and
Step-3: reacting the acidic mixture product with hydrogen in the presence of a catalyst to thereby produce a reaction product containing a tetrahydropyran compound represented by formula (2)

(2)

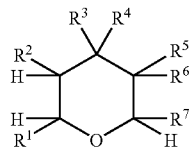

wherein all the symbols in the formulae have the same meanings as defined above.

13. The production process of a tetrahydropyran compound according to claim 12, wherein 3,4-dihydro-2-alkoxy-2H-pyran compound obtained by reacting a compound represented by formula (6)

(6)

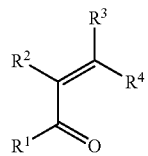

with a compound represented by formula (7)

(7)

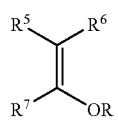

wherein all the symbols in the formulae have the same meanings as defined in claim 12.

14. The production process of a tetrahydropyran compound according to claim 13, wherein a compound represented by formula (6) is allowed to react with a compound represented by formula (7) under increased pressure.

* * * * *